(12) United States Patent
Kakinuma

(10) Patent No.: US 12,098,236 B2
(45) Date of Patent: Sep. 24, 2024

(54) MONOMER COMPOSITION AND PRODUCTION METHOD THEREOF, RAW MATERIAL COMPOSITION, CURABLE COMPOSITION, AND MOLDED BODY

(71) Applicant: MITSUI CHEMICALS, INC., Tokyo (JP)

(72) Inventor: Naoyuki Kakinuma, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 596 days.

(21) Appl. No.: 17/298,044

(22) PCT Filed: Dec. 10, 2019

(86) PCT No.: PCT/JP2019/048264
§ 371 (c)(1),
(2) Date: May 28, 2021

(87) PCT Pub. No.: WO2020/122059
PCT Pub. Date: Jun. 18, 2020

(65) Prior Publication Data
US 2022/0098356 A1    Mar. 31, 2022

(30) Foreign Application Priority Data

Dec. 12, 2018 (JP) ................................. 2018-232722

(51) Int. Cl.
| | | |
|---|---|---|
| *C08G 18/34* | (2006.01) | |
| *A61K 6/891* | (2020.01) | |
| *A61K 6/90* | (2020.01) | |
| *C08F 290/06* | (2006.01) | |
| *C08G 18/24* | (2006.01) | |
| *C08G 18/72* | (2006.01) | |
| *C08K 5/521* | (2006.01) | |

(52) U.S. Cl.
CPC .............. *C08G 18/34* (2013.01); *A61K 6/891* (2020.01); *A61K 6/90* (2020.01); *C08F 290/067* (2013.01); *C08G 18/246* (2013.01); *C08K 5/521* (2013.01); *C08G 18/72* (2013.01)

(58) Field of Classification Search
CPC ...... C08G 18/34; C08G 18/246; C08G 18/72; A61K 6/891; A61K 6/90; C08K 5/521; C08F 290/067
See application file for complete search history.

(56) References Cited

U.S. PATENT DOCUMENTS

| | | |
|---|---|---|
| 3,825,518 A | 7/1974 | Foster et al. |
| 3,862,920 A | 1/1975 | Foster et al. |
| 4,374,937 A | 2/1983 | Nemcek et al. |
| 2018/0110683 A1* | 4/2018 | Yoshinaga ............ C07C 271/20 |

FOREIGN PATENT DOCUMENTS

| | | |
|---|---|---|
| EP | 0 301 516 A2 | 2/1989 |
| JP | S51-36960 B2 | 10/1976 |
| JP | S55-92707 A | 7/1980 |

* cited by examiner

*Primary Examiner* — Rabon A Sergent
(74) *Attorney, Agent, or Firm* — BUCHANAN, INGERSOLL & ROONEY PC

(57) ABSTRACT

A monomer composition, including: an acidic phosphoric acid ester (A); an amine-based catalyst (B); and a (meth) acrylate (E) having at least one of a urethane bond or a —NHC(=S)O— bond.

15 Claims, No Drawings

MONOMER COMPOSITION AND PRODUCTION METHOD THEREOF, RAW MATERIAL COMPOSITION, CURABLE COMPOSITION, AND MOLDED BODY

TECHNICAL FIELD

The disclosure relates to a monomer composition and a production method thereof, a raw material composition, a curable composition, and a molded body.

BACKGROUND ART

A urethane (meth)acrylate, which is a (meth)acrylate compound having a urethane bond, is known as an example of a monomer contained in a curable composition.

Conventionally, urethane (meth)acrylates have been synthesized using Sn (tin)-based catalysts.

For example, Patent Document 1 discloses a dental composite filler that is a mixture of a fine inert inorganic filler powder and a reaction product of an organic diisocyanate and an oxyalkyl acrylate or an oxyalkyl methacrylate. In the Examples of this Patent Document 1, dibutyl tin dilaurate is used as a catalyst to react oxypropyl methacrylate with 2,2,4-trimethylhexamethylene diisocyanate to form a diurethane dimethacrylate.

Patent Document 1: Japanese Examined Patent Publication (JP-B) No. S51-36960

SUMMARY OF INVENTION

Technical Problem

In recent years, from the viewpoint of reducing use amount of heavy metals, etc., there has been a demand for alternative catalysts to Sn-based catalysts (for example, dibutyl tin dilaurate (DBTDL)) for formation of urethane (meth)acrylates.

There may be cases in which the stability of urethane (meth)acrylates needs to be further improved.

These circumstances in urethane (meth)acrylates (that is, (meth)acrylates having urethane bonds (—NHC(=O)O— bonds)) are similar to those in (meth)acrylates having —NHC(=S)O— bonds.

An object of one aspect of the disclosure is to provide a monomer composition which contains a (meth)acrylate (E) having at least one of a urethane bond or a —NHC(=S)O— bond and in which the stability of the contained (meth)acrylate (E) is excellent and a production method thereof, a raw material composition that is a raw material for the above-described monomer composition, a curable composition containing the above-described monomer composition, and a molded body that is a cured product of the above-described curable composition.

Solution to Problem

A solution for the above object is as follows.
<1> A monomer composition, comprising:
an acidic phosphoric acid ester (A);
an amine-based catalyst (B); and
a (meth)acrylate (E) having at least one of a urethane bond or a —NHC(=S)O— bond.
<2> The monomer composition according to <1>, wherein the (meth)acrylate (E) is a reaction product of an iso(thio)cyanate (C) having two or more iso(thio)cyanate groups and a (meth)acrylate (D) having a hydroxy group.

<3> The monomer composition according to <2>, wherein the iso(thio)cyanate (C) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate.

<4> The monomer composition according to <2> or <3>, wherein the (meth)acrylate (D) is at least one selected from the group consisting of 2-hydroxyethyl (meth)acrylate, 2-hydroxypropyl (meth)acrylate, 2-hydroxybutyl (meth)acrylate, 2-hydroxy-3-phenoxypropyl (meth)acrylate, 4-hydroxybutyl (meth)acrylate, and 1,4-cyclohexanedimethanol mono (meth)acrylate.

<5> The monomer composition according to any one of <1> to <4>, wherein the acidic phosphoric acid ester (A) is a compound represented by the following Formula (1):

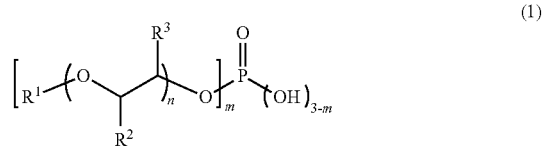

wherein, in Formula (1), m represents 1 or 2, n represents an integer from 0 to 18, $R^1$ represents a hydrogen atom or a hydrocarbon group having from 1 to 20 carbon atoms, and $R^2$ and $R^3$ each independently represent a hydrogen atom, a methyl group, or an ethyl group, provided that when $R^1$ is a hydrogen atom, n is an integer from 1 to 18.

<6> The monomer composition according to any one of <1> to <5>, wherein the amine-based catalyst (B) is at least one selected from the group consisting of the following compound (b-1), the following compound (b-2), the following compound (b-3), and the following compound (b-4):

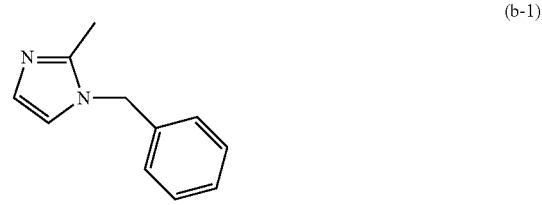

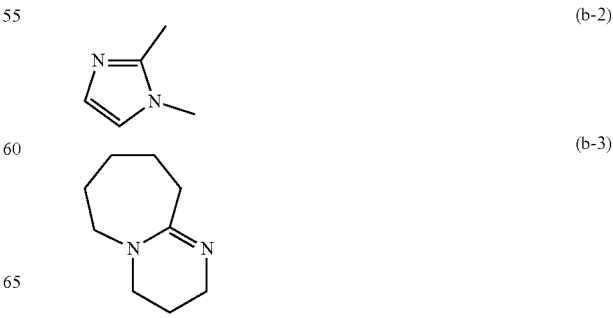

-continued

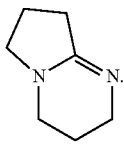

(b-4)

<7> The monomer composition according to any one of <1> to <6>, wherein a mass ratio of the acidic phosphoric acid ester (A) to the amine-based catalyst (B) is 0.7 or more.

<8> The monomer composition according to any one of <1> to <7>, wherein a viscosity at 65° C. measured by an E-type viscometer is 400,000 mPa·s or less.

<9> The monomer composition according to any one of <1> to <8>, wherein a content of an Sn-based catalyst with respect to a total amount of the monomer composition is less than 1,000 ppm by mass.

<10> A method of producing the monomer composition according to any one of <1> to <9>, the method comprising a step of mixing the acidic phosphoric acid ester (A), the amine-based catalyst (B), an iso(thio)cyanate (C) having two or more iso(thio)cyanate groups, and a (meth)acrylate (D) having a hydroxy group.

<11> A raw material composition that is a raw material for the monomer composition according to any one of <1> to <9>, the raw material composition comprising the acidic phosphoric acid ester (A), the amine-based catalyst (B), an iso(thio)cyanate (C) having two or more iso(thio)cyanate groups, and a (meth)acrylate (D) having a hydroxy group.

<12> A curable composition, comprising the monomer composition according to any one of <1> to <9>.

<13> The curable composition according to <12>, further comprising a polymerization initiator.

<14> The curable composition according to <12> or <13>, further comprising a filler.

<15> The curable composition according to any one of <12> to <14>, which is a composition for a dental material.

<16> A molded body that is a cured product of the curable composition according to any one of <12> to <15>.

Advantageous Effects of Invention

According to one aspect of the disclosure, a monomer composition which contains a (meth)acrylate (E) having at least one of a urethane bond or a —NHC(=S)O— bond and in which the stability of the contained (meth)acrylate (E) is excellent and a production method thereof, a raw material composition that is a raw material for the above-described monomer composition, a curable composition containing the above-described monomer composition, and a molded body that is a cured product of the above-described curable composition, are provided.

DESCRIPTION OF EMBODIMENTS

In the disclosure, each numerical range specified using "(from) . . . to . . . " represents a range including the numerical values noted before and after "to" as the minimum value and the maximum value, respectively.

In the disclosure, the term "step" encompasses not only an independent step, but also a step which cannot be clearly distinguished from another step, as long as an intended purpose of the step is achieved.

In the disclosure, the amount of each component in a composition means the total amount of the plurality of substances present in the composition, unless otherwise specified, when there is more than one substance corresponding to each component in the composition.

With regard to the stepwise numerical ranges described herein, the upper limit value or the lower limit value described in one numerical range may be replaced with the upper limit value or the lower limit value of another stepwise numerical range. In the numerical ranges described herein, upper limit values or lower limit values of the numerical value ranges may be replaced with values described in the Examples.

In the disclosure, "(meth)acryloyl" means acryloyl or methacryloyl, and "(meth)acrylate" means acrylate or methacrylate.

In the disclosure, "iso(thio)cyanate" means isocyanate or isothiocyanate.

[Monomer Composition]

The monomer composition of the disclosure contains an acidic phosphoric acid ester (A), an amine catalyst (B), and a (meth)acrylate (E) having at least one of a urethane bond or a —NHC(=S)O— bond.

In the monomer composition of the disclosure, the stability of the contained monomer (specifically, (meth)acrylate (E)) is excellent.

More specifically, in the monomer composition of the disclosure, the presence of a (meth)acrylate (E) together with an acidic phosphoric acid ester (A) and an amine-based catalyst (B) suppresses decomposition, polymerization, and the like of the (meth)acrylate (E), resulting in stably maintaining the (meth)acrylate (E).

<(Meth)acrylate (E)>

The monomer composition of the disclosure contains a (meth)acrylate (E) as a monomer.

The monomer composition of the disclosure may contain only one type of (meth)acrylate (E), or may contain two or more types of (meth)acrylates (E).

The monomer composition of the disclosure can be used, for example, as a component in the curable composition described below (specifically, as a supply source of monomer for the curable composition described below). The monomer composition of the disclosure itself can also be used as a curable composition.

The (meth)acrylate (E) is a (meth)acrylate having at least one of a urethane bond or a —NHC(=S)O— bond.

In the (meth)acrylate (E), the total number of urethane bonds and —NHC(=S)O— bonds is, for example, two or more.

The (meth)acrylate (E) naturally contains a (meth)acryloyl group. The total number of (meth)acryloyl groups in (meth)acrylate (E) is, for example, two or more.

One example of the (meth)acrylate (E) is a reaction product of an iso(thio)cyanate (C) having two or more iso(thio)cyanate groups and a (meth)acrylate (D) having a hydroxy group.

In the reaction to produce a (meth)acrylate (E) according to the above one example, an isocyanate group (that is, —N=C=O group) or an isothiocyanate group (that is, —N=C=S group) in an iso(thio)cyanate (C) reacts with a hydroxy group in a (meth)acrylate (D) to form a urethane bond (—NHC(=O)O-bond) or a —NHC(=S)O-bond to produce a (meth)acrylate (E).

Raw materials for the (meth)acrylate (E) in the above one example are an iso(thio)cyanate (C) having two or more iso(thio)cyanate groups and a (meth)acrylate (D) having a hydroxy group.

These raw materials will be described below.

(Iso(thio)cyanate (C))

The iso(thio)cyanate (C) has two or more iso(thio)cyanate groups.

Only one type of iso(thio)cyanate (C) or two or more types of iso(thio)cyanates (C) may be used as the raw material for the (meth)acrylate (E) in the above one example.

The number of iso(thio)cyanate groups in the iso(thio)cyanate (C) is preferably two or three, and more preferably two.

As the iso(thio)cyanate (C),
an isocyanate compound having two or more (more preferably two or three, and still more preferably two) isocyanate groups is preferable, and
at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate is more preferable.

Among the iso(thio)cyanates (C), examples of thioisocyanate compounds include: an aliphatic polyisothiocyanate compound such as hexamethylene diisothiocyanate, lysine diisothiocyanate methyl ester, lysine triisothiocyanate, m-xylylene diisothiocyanate, bis(isothiocyanatomethyl) sulfide, bis(isothiocyanatoethyl) sulfide, or bis(isothiocyanatoethyl) disulfide;

an alicyclic polyisothiocyanate compound such as isophorone diisothiocyanate, bis(isothiocyanatomethyl)cyclohexane, dicyclohexylmethane diisothiocyanate, cyclohexane diisothiocyanate, methylcyclohexane diisothiocyanate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis(isothiocyanatomethyl)tricyclodecane, or 4,9-bis(isothiocyanatomethyl)tricyclodecane; an aromatic polyisothiocyanate compound such as tolylene diisothiocyanate, 4,4-diphenylmethane diisothiocyanate, or diphenyl disulfide-4,4-diisothiocyanate; and a sulfur-containing heterocyclic polyisothiocyanate compound such as 2,5-diisothiocyanatothiophene, 2,5-bis(isothiocyanatomethyl)thiophene, 2,5-i sothiocyanatotetrahydrothiophene, 2,5-bis(isothiocyanatomethyl)tetrahydrothiophene, 3,4-bis(isothiocyanatomethyl)tetrahydrothiophene, 2,5-diisothiocyanato-1,4-dithiane, 2,5-bis(isothiocyanatomethyl)-1,4-dithiane, 4,5-diisothiocyanato-1,3-dithiolane, or 4,5-bis(isothiocyanatomethyl)-1,3-dithiolane.

((Meth)acrylate (D))

The (meth)acrylate (D) has a hydroxy group, as described above.

The (meth)acrylate (D) as a raw material for (meth)acrylate (E) in the above one example may be only one type of (meth)acrylate (D), or two or more types of (meth)acrylates (D).

The (meth)acrylate (D) is preferably at least one selected from the group consisting of 2-hydroxyethyl (meth)acrylate, 2-hydroxypropyl (meth)acrylate, 2-hydroxybutyl (meth)acrylate, 2-hydroxy-3-phenoxypropyl (meth)acrylate, 4-hydroxybutyl (meth)acrylate, and 1,4-cyclohexanedimethanol mono (meth)acrylate.

When the monomer composition of the disclosure contains the (meth)acrylate (E) (that is, the reaction product) according to the above one example, the composition may contain at least one of the iso(thio)cyanate (C) or the (meth)acrylate (D) as an unreacted raw material in addition to the (meth)acrylate (E) according to the above one example.

In the monomer composition of the disclosure, the content of the (meth)acrylate (E), with respect to the total amount of the monomer composition, is preferably 50% by mass or more, more preferably 60% by mass or more, and still more preferably 80% by mass or more.

In the monomer composition of the disclosure, the total content of (meth)acrylate (E), iso(thio)cyanate (C), and (meth)acrylate (D), with respect to the total amount of the monomer composition, is preferably 50% by mass or more, more preferably 60% by mass or more, and still more preferably 80% by mass or more.

<Acidic Phosphoric Acid Ester (A)>

The monomer composition of the disclosure contains an acidic phosphoric acid ester (A).

The monomer composition of the disclosure may contain only one type of acidic phosphoric acid ester (A) or may contain two or more types of acidic phosphoric acid esters (A).

The acidic phosphoric acid ester (A) is, in other words, a partial ester of phosphoric acid, and is a weakly acidic compound.

In the monomer composition of the disclosure, the stability of the (meth)acrylate (E) is improved by containing such an acidic phosphoric acid ester (A) together with an amine-based catalyst (B).

The acidic phosphoric acid ester (A) is preferably a compound represented by the following Formula (1).

When the monomer composition of the disclosure contains a compound represented by Formula (1), the compound represented by Formula (1) contained may be of only one type, or of two or more types.

$$\left[ R^1 \!\!-\!\! \left( O \!\!-\!\! \underset{R^2}{\overset{R^3}{\underset{|}{C}}} \!\!-\!\! \right)_{\!n} \!\! O \right]_{\!m} \!\!\!\! \overset{O}{\underset{\|}{P}} (OH)_{3-m} \quad (1)$$

In Formula (1), m represents 1 or 2, n represents an integer from 0 to 18, $R^1$ represents a hydrogen atom or a hydrocarbon group having from 1 to 20 carbon atoms, and $R^2$ and $R^3$ each independently represent a hydrogen atom, a methyl group, or an ethyl group, provided that when $R^1$ is a hydrogen atom, n is an integer from 1 to 18.

In Formula (1), n is preferably an integer from 0 to 12, more preferably an integer from 0 to 6, still more preferably an integer from 0 to 3, and still more preferably an integer from 0 to 2.

In Formula (1), when $R^1$ is a hydrogen atom, n is preferably an integer from 1 to 12, more preferably an integer from 1 to 6, still more preferably an integer from 1 to 3, and still more preferably 1 or 2.

In Formula (1), $R^1$ represents a hydrocarbon group having from 1 to 20 carbon atoms.

Examples of the hydrocarbon group include an alkyl group, an alkenyl group, an alkynyl group, an aryl group, an alkylaryl group, an alkenylaryl group, an alkynylaryl group, an arylalkyl group (also known as aralkyl group), an arylalkenyl group, and an alkynylaryl group.

Among these, an alkyl group, an alkenyl group, an aryl group, or an arylalkyl group is preferable.

The number of carbons in the hydrocarbon group represented by $R^1$ is preferably from 2 to 20, more preferably from 3 to 20, and still more preferably from 4 to 18.

In Formula (1), $R^2$ and $R^3$ each independently represent a hydrogen atom, a methyl group, or an ethyl group.

$R^2$ and $R^3$ are each independently preferably a hydrogen atom or a methyl group, and still more preferably a hydrogen atom.

<Amine-Based Catalyst (B)>

The monomer composition of the disclosure contains an amine-based catalyst (B).

The amine-based catalyst (B) contained in the monomer composition of the disclosure may be of only one type, or of two or more types.

In the monomer composition of the disclosure, the amine-based catalyst (B) cooperates with the acidic phosphoric acid ester (A) described above, and contributes to improving the stability of the (meth)acrylate (E).

The amine-based catalyst (B) may be the catalyst used in the formation of the (meth)acrylate (E) (that is, the reaction of the iso(thio)cyanate (C) with the (meth)acrylate (D)) in the above one example.

As the amine-based catalyst (B), any known amine-based catalyst can be used.

Examples of the amine-based catalyst (B) include:
an amine compound such as triethylamine, 1,4-diazabicyclo[2.2.2]octane, 2,6,7-trimethyl-1-diazabicyclo[2.2.2]octane, 1,8-diazabicyclo[5.4.0]-7-undecene, 1,5-diazabicyclo[4.3.0]-5-nonene, N,N-dimethylcyclohexylamine, pyridine, N-methylmorpholine, N,N,N',N'-tetramethylethylenediamine, N,N,N',N'-tetramethyl-1,3-butanediamine, N,N,N',N'-pentamethyldiethylenetriamine, N,N,N',N'-tetra(3-dimethylaminopropyl)-methanediamine, N,N'-dimethylpiperazine, 1,2-dimethylimidazole, or 1-benzyl-2-methylimidazole, and a salt thereof; and a trialkylphosphine compound such as tri-n-butylphosphine, tri-n-hexylphosphine, tricyclohexylphosphine, or tri-n-octylphosphine.

The amine-based catalyst (B) is particularly preferably at least one selected from the group consisting of the following compound (b-1), the following compound (b-2), the following compound (b-3), and the following compound (b-4).

Here, the compound (b-1) is 1-benzyl-2-methylimidazole (abbreviated as BMIM), the compound (b-2) is 1,2-dimethylimidazole (abbreviated as DMIM), the compound (b-3) is 1,8-diazabicyclo[5.4.0]-7-undecene (abbreviated as DBU), and the compound (b-4) is 1,5-diazabicyclo[4.3.0]-5-nonene (abbreviated as DBN).

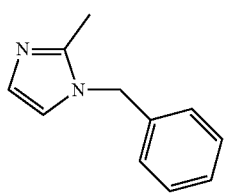

(b-1)

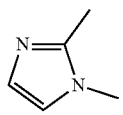

(b-2)

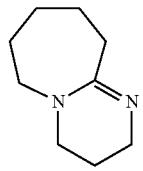

(b-3)

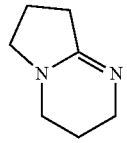

(b-4)

The mass ratio of the acidic phosphoric acid ester (A) to the amine-based catalyst (B) in the monomer composition of the disclosure (hereinafter also referred to as "mass ratio [A/B]") is not particularly limited.

The mass ratio [A/B] is preferably 0.7 or more, more preferably from 0.7 to 10, still more preferably from 0.7 to 5, and still more preferably from 1 to 3.

When the mass ratio [A/B] is 0.7 or more, the stability of the (meth)acrylate (E) is further improved.

When the mass ratio [A/B] is 10 or less, the reaction speed of the iso(thio)cyanate (C) with the (meth)acrylate (D) (that is, the formation speed of the (meth)acrylate (E)) is improved in a formation stage of the (meth)acrylate (E) in the above one example.

The total content of the acidic phosphoric acid ester (A) and the amine-based catalyst (B) in the monomer composition of the disclosure, with respect to the total content of an acidic phosphoric acid ester (A), an amine-based catalyst (B), an iso(thio)cyanate (C), a (meth)acrylate (D), and a (meth)acrylate (E), is preferably from 0.1% by mass to 10% by mass, more preferably from 0.3% by mass to 5% by mass, still more preferably from 0.3% by mass to 3% by mass and still more preferably from 0.5% by mass to 2% by mass.

<Polymerization Inhibitor>

The monomer composition of the disclosure may contain a polymerization inhibitor.

When the monomer composition of the disclosure contains a polymerization inhibitor, the monomer composition may contain only one type of polymerization inhibitor, or may contain two or more types of polymerization inhibitors.

The polymerization inhibitor is not particularly limited, and examples thereof include dibutyl hydroxytoluene (BHT), hydroquinone (HQ), hydroquinone monomethyl ether (MEHQ), and phenothiazine (PTZ).

The polymerization inhibitor content, with respect to the total content of the acidic phosphoric acid ester (A), the amine catalyst (B), the iso(thio)cyanate (C), the (meth)acrylate (D), and the (meth)acrylate (E), may be from 0.001% by mass to 0.5% by mass, from 0.002% by mass to 0.3% by mass, from 0.005% by mass to 0.3% by mass, or from 0.01% by mass to 0.2% by mass.

<Other Monomers>

The monomer composition of the disclosure may contain at least one other monomer other than the iso(thio)cyanate (C), the (meth)acrylate (D), and the (meth)acrylate (E).

Examples of the other monomer include a (meth)acrylate (hereinafter, also referred to as "(meth)acrylate (F)") other than the (meth)acrylate (E) and the (meth)acrylate (D).

Examples of the (meth)acrylate (F) include neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, and propylene oxide-modified bisphenol A di(meth)acrylate.

When the monomer composition of the disclosure contains other monomer (for example, the (meth)acrylate (F)), the content of the other monomer, with respect to the total content of the (meth)acrylate (E) and the other monomer, is preferably from 1% by mass to 70% by mass, more preferably from 5% by mass to 50% by mass, still more preferably from 10% by mass to 40% by mass, and still more preferably from 20% by mass to 40% by mass.

<Other Components>

The monomer composition of the disclosure may contain other components other than those described above.

Examples of other components that may be contained in the monomer composition of the disclosure include components in the curable composition described below.

The monomer composition of the disclosure may contain an Sn-based catalyst such as DBTDL (dibutyl tin dilaurate).

From the viewpoint of reducing the use amount of Sn, which is a heavy metal, it is preferable that the monomer composition of the disclosure does not substantially contain an Sn-based catalyst or, even if the monomer composition does contain an Sn-based catalyst, the amount of the Sn-based catalyst is reduced as much as possible.

From the above-described viewpoint, the content of the Sn-based catalyst with respect to the total amount of the monomer composition of the disclosure is preferably less than 1,000 ppm by mass (this also encompasses the case where the monomer composition of the disclosure does not contain the Sn-based catalyst).

The content of the Sn-based catalyst with respect to the total amount of the monomer composition of the disclosure is more preferably less than 100 ppm by mass, and still more preferably less than 10 ppm by mass.

The viscosity of the monomer composition of the disclosure is not particularly limited.

From the viewpoint of the treatability (handling property) of the monomer composition, the viscosity of the monomer composition of the disclosure is preferably 400,000 mPa·s or less, more preferably 100,000 mPa·s or less, still more preferably 10,000 mPa·s or less, still more preferably 1,000 mPa·s or less, and still more preferably 300 mPa·s or less.

The lower limit of the viscosity of the monomer composition of the disclosure is also not restricted, and examples of the lower limit of the viscosity include 1 mPa·s, 10 mPa·s, and 100 mPa·s.

In the disclosure, the viscosity of the monomer composition means the viscosity at 65° C. as measured by an E-type viscometer.

The same applies to the viscosity of the curable composition described below.

One Example of Method of Producing Monomer Composition (Production Method A)

The method of producing the monomer composition of the disclosure is not particularly restricted.

Hereinafter, one example of a method of producing the monomer composition of the disclosure will be described as Production Method A.

Production Method A includes a step of mixing an acidic phosphoric acid ester (A), an amine-based catalyst (B), an iso(thio)cyanate (C), and a (meth)acrylate (D) (hereinafter, also referred to as "mixing step").

Production Method A may include another step, if necessary.

In the mixing step, by mixing the acidic phosphoric acid ester (A), the amine-based catalyst (B), the iso(thio)cyanate (C), and the (meth)acrylate (D), a reaction between the iso(thio)cyanate (C) and the (meth)acrylate (D) proceeds to produce a (meth)acrylate (E) as a reaction product.

In the mixing step, an aspect of mixing components is not particularly restricted.

In a preferable aspect of mixing components, a catalyst composition is prepared at first by mixing the acidic phosphoric acid ester (A) and the amine-based catalyst (B), then iso(thio)cyanate (C) is added to the resulting catalyst composition and mixed to prepare an iso(thio)cyanate-containing composition, and the (meth)acrylate (D) is added to the resulting iso(thio)cyanate-containing composition and mixed.

The reaction temperature for the above-described reaction in the mixing step is preferably from 40° C. to 90° C., more preferably from 50° C. to 90° C., and still more preferably from 60° C. to 90° C.

The reaction time of the above-described reaction in the mixing step is, from the viewpoint of further progressing the reaction between the iso(thio)cyanate (C) and the (meth)acrylate (D), preferably 5 hours or more, more preferably 10 hours or more, still more preferably 15 hours or more, and still more preferably 20 hours or more.

The reaction time is, from the viewpoint of further suppressing decomposition and/or polymerization of the (meth)acrylate (E), preferably 50 hours or less, more preferably 40 hours or less, and still more preferably 30 hours or less.

In the mixing step, the mass ratio of the acidic phosphoric acid ester (A) to the amine-based catalyst (B) (hereinafter, also referred to as "mass ratio [A/B]") is preferably 0.7 or more, more preferably 0.7 to 10, still more preferably 0.7 to 5, and still more preferably 1 to 3.

When the mass ratio [A/B] is 0.7 or more, the stability of the formed (meth)acrylate (E) is further improved.

When the mass ratio [AB] is 10 or less, the reaction speed of the iso(thio)cyanate (C) and the (meth)acrylate (D) (that is, the formation speed of the (meth)acrylate (E)) is improved.

The total use amount of the acidic phosphoric acid ester (A) and the amine-based catalyst (B) in the mixing step, with respect to the total use amount of the acidic phosphoric acid ester (A), the amine-based catalyst (B), the iso(thio)cyanate (C), and the (meth)acrylate (D), is preferably 0.1% by mass to 10% by mass, more preferably 0.3% by mass to 5% by mass, and still more preferably 0.5% by mass to 5% by mass.

In the mixing step, the molar ratio of the hydroxy groups in the (meth)acrylate (D) to the iso(thio)cyanate groups in the iso(thio)cyanate (C) (that is, the molar ratio [hydroxy groups/iso(thio)cyanate groups]) is preferably from 0.3 to 2, more preferably from 0.5 to 1.5, still more preferably from 0.8 to 1.2, and still more preferably from 0.9 to 1.1.

The total use amount of the iso(thio)cyanate (C) and the (meth)acrylate (D) in the mixing step, with respect to the total use amount of the acidic phosphoric acid ester (A), the amine-based catalyst (B), the iso(thio)cyanate (C), and the (meth)acrylate (D), is preferably 90% by mass or more, and more preferably 95% by mass or more.

The upper limit of the total use amount of the iso(thio)cyanate (C) and the (meth)acrylate (D) is appropriately determined according to the total use amount of the acidic phosphoric acid ester (A) and the amine-based catalyst (B). Examples of the upper limit of the total use amount of the iso(thio)cyanate (C) and the (meth)acrylate (D) include 99.9% by mass, 99.7% by mass, and 99.5% by mass.

In the mixing step, not only the acidic phosphoric acid ester (A), the amine-based catalyst (B), the iso(thio)cyanate (C), and the (meth)acrylate (D), but also other component may be added and mixed.

The other component is preferably a polymerization inhibitor. For the polymerization inhibitor, the section "Monomer Composition" can be referred to as appropriate.

When a polymerization inhibitor is added and components are mixed in the mixing step, polymerization of the (meth)acrylate (D) can be more suppressed, and the reaction of the iso(thio)cyanate (C) and the (meth)acrylate (D) can proceed more effectively.

The use amount of polymerization inhibitor, with respect to the total use amount of the acidic phosphoric acid ester (A), the amine-based catalyst (B), the iso(thio)cyanate (C), and the (meth)acrylate (D), may be from 0.001% by mass to 0.5% by mass, from 0.002% by mass to 0.3% by mass, or from 0.005% by mass to 0.3% by mass.

[Raw Material Composition]

The raw material composition of the disclosure is a composition used as a raw material for the monomer composition of the disclosure, and contains an acidic phosphoric acid ester (A), an amine-based catalyst (B), an iso(thio)cyanate (C), and a (meth)acrylate (D).

The raw material composition of the disclosure is a raw material before reaction in the mixing step of Production Method A described above.

For a preferable content and the like of each component of the acidic phosphoric acid ester (A), the amine-based catalyst (B), the iso(thio)cyanate (C), and the (meth)acrylate (D), the section "One Example of Method of Producing Monomer Composition (Production Method A)" can be referred to as appropriate.

[Curable Composition]

The curable composition of the disclosure contains the monomer composition of the present described above.

In other words, the curable composition of the disclosure contains components in the monomer composition of the disclosure described above.

The curable composition of the disclosure may be composed of the monomer composition of the disclosure described above (that is, the monomer composition of the disclosure per se).

The curable composition of the disclosure are suitably used in the production of a cured product (for example, a molded body as described below). A cured product herein refers to a cured product of the curable composition of the disclosure.

Curing of the curable composition of the disclosure is achieved by polymerization of the contained monomers.

Examples of methods for curing the curable composition of the disclosure include room temperature polymerization of the monomers in the curable composition, thermal polymerization of the monomers in the curable composition, and photopolymerization of the monomers in the curable composition.

The curable composition of the disclosure has excellent mechanical properties (such as elastic modulus, breaking strength, or breaking energy) when cured.

It is believed that the above-described (meth)acrylate (E) as a monomer (that is, the (meth)acrylate (E) having at least one of a urethane bond (—NHC(=O)O— bond) or a —NHC(=S)O— bond) contributes to such effects.

It is considered that the acidic phosphoric acid ester (A) and the amine-based catalyst (B) have little effect on curing of the curable composition of the disclosure.

The content of the monomer composition in the curable composition of the disclosure, with respect to the total amount of the curable composition, is preferably 10% by mass or more, more preferably 20% by mass or more, and still more preferably 30% by mass or more.

The content of the monomer composition in the curable composition of the disclosure, with respect to the total amount of the curable composition, may be 100% by mass, 80% by mass or less, 60% by mass or less, 50% by mass or less, or the like.

<Polymerization Initiator>

The curable composition of the disclosure preferably contains a polymerization initiator.

When the curable composition of the disclosure contains a polymerization initiator, the curable composition may contain only one type of polymerization initiator, or two or more types of polymerization initiators.

When the curable composition of the disclosure contains a polymerization initiator, the polymerization of a monomer (that is, the (meth)acrylate (E) and another monomer contained as necessary; the same applies hereinafter) can be further promoted in the process of curing the curable composition.

For example, a redox polymerization initiator that combines an oxidizing agent and a reducing agent is preferable as a polymerization initiator when room temperature polymerization is carried out for polymerization of monomers.

When a redox polymerization initiator is used, for example, an oxidizing agent and a reducing agent in separately packaged forms may be prepared, and the two may be mixed immediately before use.

The oxidizing agents are not particularly restricted, and examples thereof include organic peroxides such as diacyl peroxides, peroxyesters, dialkyl peroxides, peroxyketals, ketone peroxides, and hydroperoxides.

Examples of the above-described organic peroxides include:
a diacyl peroxide such as benzoyl peroxide, 2,4-dichlorobenzoyl peroxide, or m-toluoyl peroxide;
a peroxyl ester such as t-butyl peroxy benzoate, bis-t-butyl peroxy isophthalate, 2,5-dimethyl-2,5-bis(benzoyl peroxy)hexane, t-butyl peroxy-2-ethylhexanoate, or t-butyl peroxy isopropyl carbonate;
a dialkyl peroxide such as dicumyl peroxide, di-t-butyl peroxide, or lauroyl peroxide;
a peroxyketal such as 1,1-bis(t-butylperoxy)-3,3,5-trimethylcyclohexane;
a ketone peroxide such as methyl ethyl ketone peroxide; and
a hydroperoxide such as t-butyl hydroperoxide.

The reducing agent is not particularly limited, and a tertiary amine is usually used.

Examples of the tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis (2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylaminobenzoate, 2-butoxyethyl 4-dimethylaminobenzoate, (2-methacryloyloxy)ethyl 4-dimethylaminobenzoate, trimethylamine, triethylamine, N-methyldiethanolamine, N-ethyl diethanolamine, N-n-butyl diethanolamine, N-lauryl diethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine, and tris(methacryloyloxyethyl)amine.

In addition to these organic peroxide/amine-based polymerization initiators, a redox polymerization initiator such as a cumene hydroperoxide/thiourea-based polymerization initiator, an ascorbic acid/$Cu^{2+}$ salt-based polymerization initiator, or an organic peroxide/amine/sulfinic acid (or a salt thereof)-based polymerization initiator can be used.

As a polymerization initiator, tributylborane or organic sulfinic acid is also suitably used.

When thermal polymerization by heating is performed for polymerization of monomers, a peroxide, an azo compound, or the like is preferable as a polymerization initiator.

The peroxide is not particularly limited, and examples thereof include benzoyl peroxide, t-butyl hydroperoxide, and cumene hydroperoxide.

The azo compound is not particularly limited, and examples thereof include azobisisobutyronitrile.

For a polymerization initiator (hereinafter, also referred to as "photopolymerization initiator") when photopolymerization by visible light irradiation is performed for polymerization of monomers, a redox initiator such as α-diketone/tertiary amine, α-diketone/aldehyde, or α-diketone/mercaptan is preferable.

The photopolymerization initiator is not particularly limited, and examples thereof include an α-diketone/reducing agent, a ketal/reducing agent, and a thioxanthone/reducing agent.

Examples of the α-diketone include camphorquinone, benzil, and 2,3-pentanedione.

Examples of the ketal include benzyl dimethyl ketal and benzyl diethyl ketal.

Examples of the thioxanthone include 2-chlorothioxanthone and 2,4-diethyl thioxanthone.

Examples of the reducing agent include:
a tertiary amine such as Michler Ketone, 2-(dimethylamino)ethyl methacrylate, N,N-bis[(meth)acryloyloxyethyl]-N-methylamine, ethyl N,N-dimethylaminobenzoate, butyl 4-dimethylaminobenzoate, 2-butoxyethyl 4-dimethylaminobenzoate, N-methyldiethanolamine, 4-dimethylaminobenzophenone, N,N-bis(2-hydroxyethyl)-p-toluidine, or dim ethylaminophenanthol;
an aldehyde such as citronellal, laurylaldehyde, phthaldialdehyde, dimethylaminobenzaldehyde, or terephthalaldehyde; and
a compound having a thiol group such as 2-mercaptobenzoxazole, decanethiol, 3-mercaptopropyltrimethoxysilane, 4-mercaptoacetophenone, thiosalicylic acid, or thiobenzoic acid.

Furthermore, an initiator such as an a-diketone/organic peroxide/reducing agent or the like-based initiator, in which an organic peroxide is added to these redox initiators, is also suitably used.

When photopolymerization is performed by ultraviolet irradiation, a photopolymerization initiator such as benzoin alkyl ether or benzyl dimethyl ketal is preferred. Photopolymerization initiators such as (bis)acylphosphine oxides are also suitably used.

Among the (bis)acylphosphine oxides, examples of acylphosphine oxides include 2,4,6-trimethylbenzoyl diphenylphosphine oxide, 2,6-dimethoxybenzoyl diphenylphosphine oxide, 2,6-dichlorobenzoyl diphenylphosphine oxide, 2,4,6-trimethylbenzoylmethoxyphenylphosphine oxide, 2,4,6-trimethylbenzoyl ethoxyphenylphosphine oxide, 2,3,5,6-tetramethylbenzoyl diphenylphosphine oxide, or benzoyl di-(2,6-dimethylphenyl)phosphonate.

Examples of bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

These (bis)acylphosphine oxides photoinitiators may be used singly or in combination with a reducing agent such as an amine, an aldehyde, a mercaptan, or a sulfinate.

These (bis)acylphosphine oxides photoinitiators may also be used in combination with the above-described visible light photoinitiators.

The content of the polymerization initiator, with respect to the total amount of monomers contained in the curable composition, is preferably from 0.01% by mass to 20% by mass, and more preferably from 0.1% by mass to 5% by mass.

<Filler>

The curable composition of the disclosure preferably contains a filler.

When the curable composition of the disclosure contains a filler, the curable composition may contain only one type of filler or two or more types of fillers.

When the curable composition of the disclosure contains a filler, the mechanical properties of the curable composition when cured are further improved.

Fillers are broadly classified into organic fillers and inorganic fillers.

Examples of organic fillers include fine powders of polymethyl methacrylate, polyethyl methacrylate, methyl methacrylate-ethyl methacrylate copolymer, cross-linked polymethyl methacrylate, cross-linked polyethyl methacrylate, ethylene-vinyl acetate copolymer, and styrene-butadiene copolymer.

Examples of inorganic fillers include fine powders of various types of glasses (mainly composed of silicon dioxide and, if necessary, containing oxides of heavy metals, boron, aluminum, or the like), various ceramics, diatomaceous earth, kaolin, clay minerals (montmorillonite and the like), activated clay, synthetic zeolite, mica, calcium fluoride, ytterbium fluoride, calcium phosphate, barium sulfate, zirconium dioxide, titanium dioxide, and hydroxyapatite.

Specific examples of inorganic fillers include barium borosilicate glass (KIMBLE RAYSORB T3000, SCHOTT 8235, SCHOTT GM27884, SCHOTT GM39923, and the like), strontium boroaluminosilicate glass (RAYSORB T4000, SCHOTT G018-093, SCHOTT GM32087, and the like), lanthanum glass (SCHOTT GM31684 and the like), fluoroaluminosilicate glass (SCHOTT G018-091, SCHOTT G018-117, and the like), and boroaluminosilicate glass containing zirconium, cesium, or the like (SCHOTT G018-307, G018-308, G018-310, and the like).

For the filler, an organic-inorganic composite filler obtained by adding a polymerizable compound to an inorganic filler in advance, making the filler into a paste, polymerizing and curing the paste, and then grinding the cured product may be used.

For the inorganic filler, a microfiller with a particle diameter of 0.1 μm or less may be used.

Silica (such as one of the trade name: AEROSIL), alumina, zirconia, or titania is preferable for the material of the microfiller with a particle diameter of 0.1 μm or less.

Containing such inorganic fillers with small particle size is advantageous in obtaining abrasive smoothness of a cured product.

A filler may be surface treated with a surface treatment agent such as a silane coupling agent, depending on the purpose.

As the surface treatment agent, a known silane coupling agent such as a organosilicon compound such as methacryloxyalkyltrimethoxysilane (the number of carbon atoms between the methacryloxy group and the silicon atom: from 3 to 12), methacryloxyalkyltriethoxysilane (the number of carbon atoms between the methacryloxy group and the silicon atom: from 3 to 12), vinyltrimethoxysilane, vinylethoxysilane, or vinyltriacethoxysilane is used.

The amount of the surface treatment agent, with respect to 100% by mass of the filler before surface treatment, is preferably from 0.1% by mass to 20% by mass, and more preferably from 1% by mass to 10% by mass.

The content of a filler based on 100 parts by mass of the total amount of monomers contained in a curable composition is preferably from 10 parts by mass to 2,000 parts by mass, more preferably from 50 parts by mass to 1,000 parts by mass, and still more preferably from 100 parts by mass to 600 parts by mass.

<Other Components>

The curable composition of the disclosure may contain other component other than the above-described components.

Examples of the other component include a pigment, a dye, a bactericide, a disinfectant, a stabilizer, and a preservative.

The curable composition of the disclosure may contain an Sn-based catalyst such as DBTDL (dibutyl tin dilaurate).

From the viewpoint of reducing the use amount of Sn, which is a heavy metal, the curable composition of the disclosure is preferably substantially free of Sn-based catalysts or, even when the composition contains an Sn-based catalyst, the content of the Sn-based catalyst is preferably reduced as much as possible.

From the viewpoint described above, the content of the Sn-based catalyst with respect to the total amount of the curable composition of the disclosure is preferably less than 1,000 ppm by mass (encompassing the case where the curable composition of the disclosure does not contain an Sn-based catalyst).

The content of the Sn-based catalyst based on the total amount of the curable composition of the disclosure is more preferably less than 100 ppm by mass, and still more preferably less than 10 ppm by mass.

The viscosity of the curable composition of the disclosure is not particularly limited.

From the viewpoint of the treatability (handling property) of the curable composition, the viscosity of the curable composition of the disclosure is preferably 400,000 mPa·s or less, more preferably 100,000 mPa·s or less, still more preferably 10,000 mPa·s or less, still more preferably 1,000 mPa·s or less, and still more preferably 300 mPa·s or less.

The lower limit of the viscosity of the curable composition of the disclosure is also not restricted, and examples of the lower limit of the viscosity include 1 mPa·s, 10 mPa·s, and 100 mPa·s.

<Preferred Applications>

Applications of the curable compositions of the disclosure are not particularly restricted.

The curable composition of the disclosure can be used, for example, as paints, compositions for forming coating films, compositions for dental materials, and the like.

Since the curable composition of the disclosure can form a cured product having excellent mechanical properties, the curable composition is particularly suitable as a composition for a dental material.

Here, a composition for a dental material means such a composition that the composition per se, a cured product (for example, a molded body as described below) of the composition, or the above-described cured product that has been further processed can be used as a dental material.

Examples of dental materials include dental restorative materials, denture base resins, denture base backing materials, impression materials, materials for cohesion (resin cements, resin-modified glass ionomer cements, or the like), dental bonding materials (orthodontic bonding materials, cavity application bonding materials, or the like), dental fissure sealants, resin blocks for CAD/CAM, temporary crowns, and artificial tooth materials.

Examples of the dental restorative materials include composite resins for crowns, composite resins for caries cavity filling, composite resins for abutment construction, and composite resins for filling and restoration.

<One Example of Production Method>

The production method for producing the curable composition of the disclosure is not particularly restricted.

One example of a method of producing the curable composition of the disclosure will be described below as Production Method B.

Production Method B includes a step of preparing the monomer composition of the disclosure, and a step of mixing the monomer composition with other components (for example, polymerization initiators, and fillers).

Production Method B may include another step, if necessary.

[Molded Body]

The molded body of the disclosure is a cured product of the curable composition of the disclosure described above.

Accordingly, the molded body of the disclosure has excellent mechanical properties.

A molded body is produced, for example, by molding the curable composition of the disclosure into a desired shape and then curing the molded composition.

Examples of methods for curing the curable compositions of the disclosure are as described above.

EXAMPLES

Examples of the disclosure are shown below, but the disclosure is not limited to the following Examples.

Example 1

<Production of Monomer Composition A>

Butoxyethyl acid phosphate (hereinafter, referred to as "Compound (a-1)") (2.0 g) as an acidic phosphoric acid ester (A) and Compound (b-1) (1.0 g) as an amine-based catalyst (B) were added into a 10-mL screw vial, and mixed and dissolved at 70° C. until a homogeneous solution was obtained, thereby obtaining a catalyst composition (3.0 g).

The above-described catalyst composition (0.6 parts by mass; hereinafter, also referred to as "use amount [A+B]"), BHT (dibutyl hydroxytoluene) as polymerization inhibitor (0.025 parts by mass), and TMHDI (mixture of 2,2,4-trimethylhexamethylene diisocyanate and 2,4,4-trimethylhexamethylene diisocyanate) as an iso(thio)cyanate (C) (21.35 parts by mass) were charged into a 100-mL four-necked flask equipped with a sufficiently dried stirring blade and a thermometer, and dissolved to form a homogeneous solution.

The temperature of the resulting solution was raised to 80° C., where HEMA (hydroxyethyl methacrylate) (26.56 parts by mass) as a (meth)acrylate (D) was added dropwise over a period of one hour. Since the internal temperature rose due to reaction heat during the drop, the drop amount was controlled so that the temperature became 90° C. or lower.

After dropping the entire amount of HEMA, the reaction was carried out for 23 hours with the reaction temperature maintained at 90° C. The reaction here refers to a reaction between TMHDI and HEMA. The progress of the reaction was followed by high-performance liquid chromatography (HPLC) analysis to confirm the endpoint of the reaction.

As a result of the above, Monomer Composition A containing a urethane dimethacrylate (e-1) as the (meth)acrylate (E) was obtained.

Here, the urethane dimethacrylate (e-1) is a reaction product of TMHDI and HEMA.

Compound (a-1) and Compound (b-1) remained in Monomer Composition A. In other words, Monomer Composition A is one example of the monomer composition of the disclosure.

<Measurement of Viscosity of Monomer Composition A>

The viscosity of Monomer Composition A immediately after the 23-hour reaction described above was measured.

The above-described viscosity was measured using an E-type viscometer (TVE-22H manufactured by Toki Sangyo Co., Ltd.) while the temperature of Monomer Composition A was controlled at 65° C.

The results are shown in Table 1.

<Measurement of Refractive Index of Monomer Composition A>

The refractive index of Monomer Composition A immediately after the 23-hour reaction described above was measured.

The above-described refractive indices were measured using an Abbe-type full digital refractometer (ABBEMAT 550 manufactured by Anton Paar GmbH) while the temperature of Monomer Composition A was controlled at 25° C.

The results are shown in Table 1.

<Confirmation of Stability of (Meth)acrylate (E) in Monomer Composition A>

Immediately after the 23-hour reaction described above, the HPLC purity (area %) of the (meth)acrylate (E) in Monomer Composition A was determined by HPLC analysis, and the result obtained was designated as HPLC1 (area %).

Next, Monomer Composition A after the 23-hour reaction described above was heated at a heating temperature of 100° C. for 24 hours. The HPLC purity (area %) of the (meth)acrylate (E) in Monomer Composition A after heating was determined, and the result obtained was designated as HPLC2 (area %).

Based on HPLC1 and HPLC2, the HPLC difference was determined as an indicator of the stability of the (meth)acrylate (E) in Monomer Composition A using the following Formula.

HPLC difference (area %)=HPLC1 (area %)−HPLC2 (area %)

HPLC1 (area %), HPLC2 (area %), and HPLC difference (area %) are shown in Table 1.

The smaller the HPLC difference (area %), the better the stability of the (meth)acrylate (E) in Monomer Composition A.

Measurement of HPLC1 (area %) and HPLC2 (area %) was carried out using a solution of Curable Composition A dissolved in $CH_3CN$ and an eluent of mixture in the ratio of $CH_3CN/H_2O$=90/10 (volume ratio).

"LC-20AT" manufactured by Shimadzu Corporation was used as an HPLC system.

<Production of Monomer Composition B>

Monomer Composition A (10.5 g) immediately after the above-described 23-hour reaction and triethylene glycol dimethacrylate (abbreviated as 3G) (4.5 g) as a (meth)acrylate (F) were placed in a container, and the two were mixed by stirring at 50° C. to obtain Monomer Composition B.

The obtained Monomer Composition B is also one example of the monomer composition of the disclosure.

<Production of Curable Composition>

To Monomer Composition B (10 parts by mass), camphorquinone (abbreviated as CQ) (0.05 parts by mass) and 2-butoxyethyl 4-dimethylaminobenzoate (abbreviated as DMAB2-BE) (0.05 parts by mass) were added and stirred at room temperature until the mixture became uniform, and then 15 parts by weight of silica glass (FUSELEX-X (Tatsumori Ltd.)) as a filler was blended and stirred using a mortar until the mixture became uniform.

The resulting mixture was defoamed to obtain a curable composition.

CQ and DMAB2-BE are polymerization initiators.

<Production of Cured Product (Test Piece)>

The resulting curable composition was filled into a through hole of a stainless steel mold with a through hole with a size of 25 mm (length)×2 mm (width)×2 mm (through length). The cured composition filled in the mold was irradiated with visible light for 3 minutes on each side (that is, 6 minutes on both sides) using a visible light irradiation device (SOLIDILITE V manufactured by SHOFU Inc.) to obtain a cured product with a size of 25 mm×2 mm×2 mm.

The resulting cured product was removed from the mold, and the removed cured product was heat-treated in an oven at 130° C. for 2 hours. The cured product after heat treatment was cooled to room temperature, and the cooled cured product was immersed in distilled water in a sealable sample bottle and kept at 37° C. for 24 hours.

The cured product, which was kept for 24 hours, was used as a test piece.

<Mechanical Properties of Cured Protuct (Bending Test)>

Using the above-described test pieces and a testing machine (Autograph EZ-S manufactured by Shimadzu Corporation), a three-point bending test was conducted at a distance of 20 mm between the fulcrums and a crosshead speed of 1 mm/min, and the elastic modulus (MPa), the breaking strength (MPa), and the breaking energy (mJ) were determined as the mechanical properties of the test pieces, respectively.

The results are shown in Table 1.

Examples 2 to 15

In production of Monomer Composition A, the same operations as in Example 1 were carried out except that the combination of the type of the acidic phosphoric acid ester (A), the type of the amine-based catalyst (B), and the mass ratio [AB] (that is, the mass ratio of the acidic phosphoric acid ester (A) to the amine-based catalyst (B)) were changed as shown in Table 1.

The amount of catalyst composition used (that is, the total amount of the acidic phosphoric acid ester (A) and the amine-based catalyst (B): 0.6 parts by mass; the use amount [A+B]) was the same as in Example 1.

The results are shown in Table 1.

Comparative Example 1

In production of Monomer Composition A, the same operations as in Example 1 were carried out except that the catalyst composition (0.6 parts by mass) was changed to DBTDL (dibutyl tin dilaurate), which is an Sn-based catalyst (0.1 parts by mass), the amount of TMHDI (21.35 parts by mass) was changed to 22.34 parts by mass, and the amount of HEMA (26.56 parts by mass) was changed to 27.66 parts by mass.

The results are shown in Table 1.

Comparative Example 2

In production of Monomer Composition A, the same operation as in Example 1 was carried out except that the acidic phosphoric acid ester (A) was not used and the catalyst composition (0.6 parts by mass) was changed to the amine-based catalyst (B) (0.6 parts by mass).

The results are shown in Table 1.

In Comparative Example 2, since polymerization solidification occurred during a reaction to form a (meth)acrylate (E), the evaluations of the properties of Monomer Composition A and the mechanical properties of a cured product were unable to be performed.

TABLE 1

| | Production conditions for Monomer Composition A | | | | | | Properties of Monomer Composition A | |
|---|---|---|---|---|---|---|---|---|
| | Acidic phosphoric acid ester (A) | Amine-based catalyst (B) | Mass ratio [A/B] | Use amount [A + B] (parts by mass) | Type of Sn-based catalyst | Use amount of Sn-based catalyst (parts by mass) | Viscosity (mPa · S) | Refractive index |
| Example 1 | a-1 | b-1 | 2.0 | 0.6 | — | 0 | 180 | 1.48 |
| Example 2 | a-1 | b-1 | 3.0 | 0.6 | — | 0 | 170 | 1.48 |
| Example 3 | a-1 | b-1 | 1.0 | 0.6 | — | 0 | 170 | 1.48 |
| Example 4 | a-1 | b-2 | 2.0 | 0.6 | — | 0 | 180 | 1.48 |
| Example 5 | a-1 | b-3 | 2.0 | 0.6 | — | 0 | 170 | 1.48 |
| Example 6 | a-1 | b-4 | 2.0 | 0.6 | — | 0 | 170 | 1.48 |
| Example 7 | a-2 | b-1 | 2.0 | 0.6 | — | 0 | 170 | 1.48 |
| Example 8 | a-2 | b-4 | 2.0 | 0.6 | — | 0 | 180 | 1.48 |
| Example 9 | a-3 | b-1 | 2.0 | 0.6 | — | 0 | 170 | 1.48 |
| Example 10 | a-3 | b-4 | 2.0 | 0.6 | — | 0 | 180 | 1.48 |
| Example 11 | a-4 | b-1 | 2.0 | 0.6 | — | 0 | 170 | 1.48 |
| Example 12 | a-5 | b-1 | 2.0 | 0.6 | — | 0 | 170 | 1.48 |
| Example 13 | a-6 | b-1 | 2.0 | 0.6 | — | 0 | 180 | 1.48 |
| Example 14 | a-7 | b-1 | 2.0 | 0.6 | — | 0 | 170 | 1.48 |
| Example 15 | a-8 | b-1 | 2.0 | 0.6 | — | 0 | 180 | 1.48 |
| Comparative Example 1 | — | — | — | 0 | DBTDL | 0.1 | 170 | 1.48 |
| Comparative Example 2 | — | b-1 | 0 | 0.6 | — | 0 | N.D. (polymerization solidification during reaction) | |

| | Properties of Monomer Composition A | | | Mechanical properties of cured product of curable composition | | |
|---|---|---|---|---|---|---|
| | HPLC1 (area %) | HPLC2 (area %) | HPLC difference (=HPLC1 − HPLC2) (area %) | Elastic modulus (MPa) | Breaking strength (MPa) | Breaking energy (mJ) |
| Example 1 | 96.0 | 95.6 | 0.4 | 7940 | 181 | 30 |
| Example 2 | 95.8 | 95.6 | 0.2 | 7920 | 181 | 30 |
| Example 3 | 96.2 | 95.8 | 0.4 | 7990 | 182 | 31 |
| Example 4 | 95.2 | 95.1 | 0.1 | 7900 | 174 | 29 |
| Example 5 | 95.9 | 95.6 | 0.3 | 8040 | 179 | 30 |
| Example 6 | 95.7 | 95.4 | 0.3 | 7990 | 183 | 31 |
| Example 7 | 95.6 | 95.3 | 0.3 | 7960 | 176 | 30 |
| Example 8 | 95.6 | 95.2 | 0.4 | 7910 | 173 | 29 |
| Example 9 | 95.0 | 94.8 | 0.2 | 8020 | 178 | 31 |
| Example 10 | 95.1 | 94.7 | 0.4 | 7880 | 173 | 29 |
| Example 11 | 95.5 | 95.3 | 0.2 | 7990 | 181 | 31 |

TABLE 1-continued

| | | | | | | |
|---|---|---|---|---|---|---|
| Example 12 | 95.6 | 95.3 | 0.3 | 8000 | 178 | 30 |
| Example 13 | 95.4 | 95.3 | 0.1 | 7960 | 178 | 30 |
| Example 14 | 95.6 | 95.4 | 0.2 | 7940 | 176 | 29 |
| Example 15 | 95.5 | 95.3 | 0.2 | 8020 | 178 | 30 |
| Comparative Example 1 | 96.0 | 93.0 | 3.0 | 7960 | 178 | 30 |
| Comparative Example 2 | N.D. (polymerization solidification during reaction) | | | N.D. | | |

DESCRIPTION OF ABBREVIATIONS IN TABLE 1 a-1: Butoxyethyl acid phosphate
a-2: Diethylene glycol monolauryl ether acid phosphate
a-3: Diethylene glycol monooleyl ether acid phosphate
a-4: Butyl acid phosphate
a-5: Octyl acid phosphate
a-6: 2-ethylhexylacid phosphate
a-7: Phenylacid phosphate
a-8: Benzyl acid phosphate
(a-1 to a-8 are all compounds represented by Formula (1))
b-1: 1-benzyl-2-methyl imidazole (abbreviated as BMIM)
b-2: 1, 2-dimethyl imidazole (abbreviated as DMIM)
b-3: 1, 8-diazabicyclo [5.4.0]-7-undecene (abbreviated as DBU)
b-4: 1, 5-diazabicyclo [4.3.0]-5-nonene (abbreviated as DBN)
N.D.: No measurement results.

As shown in Table 1, in Monomer Composition A of Examples 1 to 15 containing the acidic phosphoric acid ester (A), the amine-based catalyst (B), and the (meth)acrylate (E), the HPLC difference (area %) (=HPLC1−HPLC2) was reduced compared to Monomer Composition A of Comparative Example 1. In other words, in Examples 1 to 15, it was confirmed that the stability of the (meth)acrylate (E) in Monomer Composition A was superior to that in Comparative Example 1.

In Examples 1 to 15, it was confirmed that the viscosity and refractive index of Monomer Composition A, as well as the mechanical properties of a cured product, were maintained at levels almost equivalent to those of the properties in Comparative Example 1.

In contrast, in Comparative Example 1, in which the acidic phosphoric acid ester (A) and the amine-based catalyst (B) were changed to an Sn-based catalyst, the stability of the (meth)acrylate (E) in Monomer Composition A was reduced.

In Comparative Example 2, in which the acidic phosphoric acid ester (A) was not used, polymerization solidification occurred during a reaction to form the (meth) acrylate (E). In other words, in Comparative Example 2, the stability of the (meth)acrylate (E) in Monomer Composition A was considerably reduced.

The disclosure of Japanese Patent Application No. 2018-232722, filed Dec. 12, 2018, is incorporated herein by reference in its entirety.

All documents, patent applications, and technical standards described in this specification are incorporated herein by reference to the same extent as if each individual document, patent application, or technical standard was specifically and individually indicated to be incorporated by reference.

The invention claimed is:

1. A monomer composition, comprising:
an acidic phosphoric acid ester (A);
an amine-based catalyst (B); and
a (meth)acrylate (E) having at least one of a urethane bond or a —NHC(=S)O— bond,
wherein the monomer composition does not contain an Sn-based catalyst, and
wherein the acidic phosphoric acid ester (A) is a compound represented by the following Formula (1):

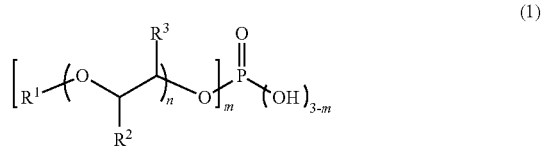

wherein, in Formula (1), m represents 1 or 2, n represents an integer from 0 to 18, $R^1$ represents a hydrogen atom or a hydrocarbon group having from 1 to 20 carbon atoms, and $R^2$ and $R^3$ each independently represent a hydrogen atom, a methyl group, or an ethyl group, provided that when $R^1$ is a hydrogen atom, n is an integer from 1 to 18.

2. The monomer composition according to claim 1, wherein the (meth)acrylate (E) is a reaction product of an iso(thio)cyanate (C) having two or more iso(thio)cyanate groups and a (meth)acrylate (D) having a hydroxy group.

3. The monomer composition according to claim 2, wherein the iso(thio)cyanate (C) is at least one selected from the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate.

4. The monomer composition according to claim 2, wherein the (meth)acrylate (D) is at least one selected from the group consisting of 2-hydroxyethyl (meth)acrylate, 2-hydroxypropyl (meth)acrylate, 2-hydroxybutyl (meth) acrylate, 2-hydroxy-3-phenoxypropyl (meth)acrylate, 4-hydroxybutyl (meth)acrylate, and 1,4-cyclohexanedimethanol mono (meth)acrylate.

5. The monomer composition according to claim 1, wherein the amine-based catalyst (B) is at least one selected from the group consisting of the following compound (b-1), the following compound (b-2), the following compound (b-3), and the following compound (b-4):

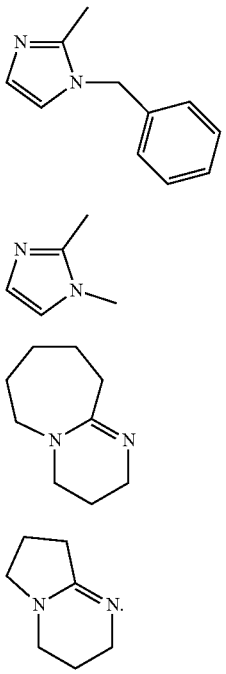

(b-1)

(b-2)

(b-3)

(b-4)

6. The monomer composition according to claim 1, wherein a mass ratio of the acidic phosphoric acid ester (A) to the amine-based catalyst (B) is 0.7 or more.

7. The monomer composition according to claim 1, wherein a viscosity at 65° C. measured by an E-type viscometer is 400,000 mPa·s or less.

8. The monomer composition according to claim 1, wherein a content of an Sn-based catalyst with respect to a total amount of the monomer composition is less than 1,000 ppm by mass.

9. A method of producing the monomer composition according to claim 1, the method comprising a step of mixing the acidic phosphoric acid ester (A), the amine-based catalyst (B), an iso(thio)cyanate (C) having two or more iso(thio)cyanate groups, and a (meth)acrylate (D) having a hydroxy group.

10. A raw material composition that is a raw material for the monomer composition according to claim 1, the raw material composition comprising the acidic phosphoric acid ester (A), the amine-based catalyst (B), an iso(thio)cyanate (C) having two or more iso(thio)cyanate groups, and a (meth)acrylate (D) having a hydroxy group, wherein the raw material composition does not contain an Sn-based catalyst.

11. A curable composition, comprising the monomer composition according to claim 1, wherein the curable composition does not contain an Sn-based catalyst.

12. The curable composition according to claim 11, further comprising a polymerization initiator.

13. The curable composition according to claim 11, further comprising a filler.

14. The curable composition according to claim 11, which is a composition for a dental material.

15. A molded body that is a cured product of the curable composition according to claim 11.

* * * * *